US008632809B2

(12) United States Patent
Asgharian et al.

(10) Patent No.: US 8,632,809 B2
(45) Date of Patent: Jan. 21, 2014

(54) WATER INSOLUBLE POLYMER MATRIX FOR DRUG DELIVERY

(75) Inventors: Bahram Asgharian, Arlington, TX (US); Masood A. Chowhan, Arlington, TX (US); Martin B. Wax, Westlake, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 1379 days.

(21) Appl. No.: 11/936,914

(22) Filed: Nov. 8, 2007

(65) Prior Publication Data

US 2008/0113027 A1 May 15, 2008

Related U.S. Application Data

(60) Provisional application No. 60/858,004, filed on Nov. 9, 2006.

(51) Int. Cl.
*A61K 9/14* (2006.01)
*A61K 47/30* (2006.01)

(52) U.S. Cl.
USPC ........................................ 424/484; 514/772.3

(58) Field of Classification Search
USPC ........................................ 424/484; 514/772.3
See application file for complete search history.

(56) References Cited

U.S. PATENT DOCUMENTS

| | | | |
|---|---|---|---|
| 2,798,053 A | 7/1957 | Brown | 260/2.2 |
| 3,755,560 A | 8/1973 | Dickert et al. | 424/78 |
| 3,949,750 A | 4/1976 | Freeman | |
| 4,079,038 A | 3/1978 | Choi et al. | 260/47 XA |
| 4,093,709 A | 6/1978 | Choi et al. | 424/19 |
| 4,131,648 A | 12/1978 | Choi et al. | 424/22 |
| 4,138,344 A | 2/1979 | Choi et al. | 252/1 |
| 4,180,646 A | 12/1979 | Choi et al. | 528/153 |
| 4,304,767 A | 12/1981 | Heller et al. | 424/78 |
| 4,421,769 A | 12/1983 | Dixon et al. | 424/358 |
| 4,474,753 A | 10/1984 | Haslam et al. | 424/78 |
| 4,478,822 A | 10/1984 | Haslam et al. | 424/78 |
| 4,509,949 A | 4/1985 | Huang et al. | 586/558 |
| 4,599,379 A | 7/1986 | Flesher et al. | 524/801 |
| 4,628,078 A | 12/1986 | Glover et al. | 526/303.1 |
| 4,745,160 A | 5/1988 | Churchill et al. | 525/415 |
| 4,835,206 A | 5/1989 | Farrar et al. | 524/457 |
| 4,849,484 A | 7/1989 | Heard | 525/221 |
| 4,946,931 A | 8/1990 | Heller et al. | 528/230 |
| 4,957,998 A | 9/1990 | Heller et al. | 528/220 |
| 5,011,681 A | 4/1991 | Ciotti et al. | 424/81 |
| 5,013,821 A | 5/1991 | Heller et al. | 528/376 |
| 5,019,400 A | 5/1991 | Gombotz et al. | 424/497 |
| 5,030,457 A | 7/1991 | Ng et al. | 424/486 |
| 5,087,445 A | 2/1992 | Haffey et al. | 424/59 |
| 5,100,660 A | 3/1992 | Hawe et al. | 424/78.35 |
| 5,171,270 A | 12/1992 | Herrick | 623/11 |
| 5,283,063 A | 2/1994 | Freeman | 424/427 |
| 5,469,867 A | 11/1995 | Schmitt | 128/898 |
| 5,575,815 A | 11/1996 | Slepian et al. | |
| 5,648,506 A | 7/1997 | Desai et al. | 549/510 |
| 5,702,716 A * | 12/1997 | Dunn et al. | 424/422 |
| 5,723,005 A | 3/1998 | Herrick | 623/4 |
| 5,824,343 A | 10/1998 | Ng et al. | 424/486 |
| 5,939,453 A | 8/1999 | Heller et al. | 514/452 |
| 5,962,006 A * | 10/1999 | Southard et al. | 424/426 |
| 6,004,753 A | 12/1999 | Yue et al. | 435/6 |
| 6,048,522 A | 4/2000 | Plochocka et al. | 424/78.24 |
| 6,117,949 A | 9/2000 | Rathi et al. | 525/415 |
| 6,201,072 B1 | 3/2001 | Rathi et al. | 525/415 |
| 6,372,245 B1 | 4/2002 | Bowman et al. | 424/427 |
| 6,440,460 B1 | 8/2002 | Gurny et al. | |
| 6,565,874 B1 | 5/2003 | Dunn et al. | |
| 6,699,493 B2 * | 3/2004 | Wong | 424/428 |
| 6,995,186 B2 | 2/2006 | Castillo et al. | 514/450 |
| 2002/0182185 A1 | 12/2002 | Wong | |
| 2003/0055102 A1 | 3/2003 | Castillo et al. | 514/450 |
| 2004/0001872 A1 | 1/2004 | Shih et al. | |
| 2004/0068078 A1 | 4/2004 | Milbocker | |
| 2005/0158387 A1 | 7/2005 | Castillo et al. | 424/486 |
| 2006/0009498 A1 | 1/2006 | Whitcup | 514/357 |
| 2006/0121085 A1 | 6/2006 | Warren et al. | |
| 2006/0257451 A1 | 11/2006 | Varner et al. | |
| 2008/0114076 A1 | 5/2008 | Asgharian et al. | 514/772.3 |

FOREIGN PATENT DOCUMENTS

| | | |
|---|---|---|
| EP | 0556818 A1 | 8/1993 |
| EP | 0537559 B1 | 1/1998 |
| JP | 04364839 | 12/1992 |
| JP | 09020651 | 1/1997 |
| WO | 94/05342 | 3/1994 |
| WO | 9503036 | 2/1995 |

(Continued)

OTHER PUBLICATIONS

Winternitz et al. Pharm. Res. 1996, 13 (3), 368-375.*
Polysciences, Inc. (MSDS: poly(caprolactone) diol), May 2, 2003).*
Perstorp (MSDS: CAPA(R) 4101 and 4801, Jun. 1, 2005).*
Winternitz et al. Pharm Res 1996, 13 (3), 368-375.*
Kim et al. Journal of Industrial and Engineering Chemistry, 1998, 4 (3), 221-225.*
Perstorp, MSDS, Jun. 1, 2005.*
International PCT Search Report for corresponding PCT/US2007/084023 with mailing date Aug. 12, 2008.

(Continued)

*Primary Examiner* — Gina C Justice
*Assistant Examiner* — Genevieve S Alley
(74) *Attorney, Agent, or Firm* — Scott A. Chapple

(57) ABSTRACT

Disclosed is a pharmaceutical composition comprising (a) a bioerodible water insoluble polymer matrix comprising a polyester polymer, wherein the polymer matrix has a melting point of less than 60° C. and (b) an active agent dispersed within the polymer matrix, wherein the composition is formulated to controllably release the active agent for a pre-determined period of time to a target site. Also disclosed are methods of treating a disease or condition with the disclosed compositions.

15 Claims, 2 Drawing Sheets

(56) References Cited

FOREIGN PATENT DOCUMENTS

| WO | 9529200 | 11/1995 |
|---|---|---|
| WO | 9715287 | 5/1997 |
| WO | 02/11783 | 2/2002 |
| WO | 02/30393 | 4/2002 |
| WO | 2004/028583 | 4/2004 |
| WO | 2004081196 A2 | 9/2004 |
| WO | 2005/107706 | 11/2005 |
| WO | 2006/031658 | 3/2006 |
| WO | 2007/115259 | 10/2007 |
| WO | 2007/115261 | 10/2007 |
| WO | 2008/051757 | 5/2008 |

OTHER PUBLICATIONS

International PCT Written Opinion for corresponding PCT/US2007/084023 with mailing date Aug. 12, 2008.

EP Communication pursuant to Article 94(3) EPC [First Examination Report] for corresponding EP 07 864 085.1 with mailing date Feb. 28, 2011, which is related to U.S. Appl. No. 11/936,875.

Winternitz et al., Pharmaceutical Research, 13(3), pp. 368-375, 1996.

EP Communication for corresponding EP 07871406.0 dated Jun. 24, 2011.

EP Summons for corresponding EP Application No. 07864085.1 dated Mar. 7, 2012.

Perstorp: "CAPA 3031, 3041, 3050, 3091 and 3201 Polycaprolactones", Jan. 6, 2005, pp. 1-8, XP55003964, Retrieved from the Internet: URL:http://www.perstorppolyols.com/upload/capa3031_070420.pdf [retrieved on Aug. 1, 2011].

Resomer, "Resomer® Biodegradable Polymers for Medical Device", Retrieved from Internet: URL:http://www.signmaaldrich.com/materials-science/polymer-science/resomer.html#a4 [retrieved Jun. 15, 2011].

Solvay, "The CAPA Range of Products", Product brochure, Oct. 28, 2003, Product brochure, pp. 1-2, XP55019690, Retrieved from the internet: URL:http://www.prochem.ch/html/forum/Capa_Range_of_Product.pdf [retrieved on Feb. 17, 2012].

Tiago et al., 2004, "Metabolic and Genetic Diversity of Mesophilic and Thermophilic Bacteria Isolated from Composted Municipal Sludge on Poly-M-caprolactones", Current Microbiology, 2004, pp. 407-414, vol. 49(6).

\* cited by examiner

Erosion Study

WATER INSOLUBLE POLYMER MATRIX FOR DRUG DELIVERY

This application claims priority to U.S. Provisional Application, U.S. Ser. No. 60/858,004 filed Nov. 9, 2006.

BACKGROUND OF THE INVENTION

A. Field of the Invention

The present invention relates generally to drug delivery compositions. In particular, this invention relates to the use of liquid bioerodible materials for sustained release of an active agent by injecting to a targeted area of a subject.

B. Background of the Invention

1. Solid Drug Delivery Systems

Current drug delivery treatment options are oftentimes difficult to use and can Is be ineffective due to the inefficient delivery of an active agent to a targeted site. For instance, solid matrix (drug mixed with a solid bioerodable or non-errodable polymer) has to be surgically inserted in the targeted area. Polymers used in this area include polylactic acid, polyglycolic acid, poly ϵ-caprolactones, polyhydroxybutayrate, polyhydroxybutyrate-polyhydroxyvalerate co-polymers, among others. These polymers typically have high molecular weight typically 10,000 to 100,000 and thus are rigid polymers having high melting points above 70° C.

2. Liquid Drug Delivery Systems

Attempts to make injectable formulations typically involve using a solution of polymers in an organic solvent such as N-methylpyrrolidone (US 2006/0009498). The use of solvents can oftentimes increase the potential toxicity of the drug delivery formulation.

Injectable polymeric systems which are liquid at room temperature and do not require solvents include POE polymers. For instance, U.S. Pat. Nos. 4,079,038, 4,093,709, 4,131,648, 4,138,344 and 4,180,646 disclose drug delivery systems using bioerodible POE polymers. These polymers are formed by a reaction between an orthoester (or orthocarbonate) such as 2,2-diethoxytetrahydrofuran and a diol such as 1,4-cyclohexanedimethanol. The reaction requires elevated temperature and reduced pressure and a relatively long reaction time. Drugs or other active agents are retained in the polymer matrix to be released as the polymer biodegrades due to hydrolysis of the labile linkages. U.S. Pat. No. 4,304,767 discloses POE polymers having repeating units represented by the general formulas:

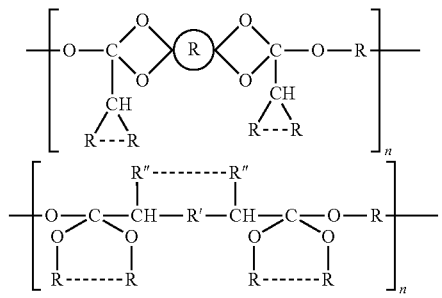

The polymers are formed by a condensation reaction between ketene acetals and hydroxyl containing compounds and have relatively higher molecular weights. A disadvantage of POE polymers is that they tend to have a relatively fast degradation time. This can render them un-suitable as long-term controlled release drug delivery vehicles.

The use of water-soluble polymers has also been used in liquid drug delivery systems. For instance, U.S. Pat. No. 5,648,506 describes a polymeric drug delivery system where an active agent is bound to a water-soluble polymer to provide a form of soluble drug delivery especially for those cases in which the drug by itself is water-insoluble. In particular, taxol is covalently bound to water-soluble polyethylene glycols with other functional monomers to comprise a form of polymeric drug delivery. A disadvantage of water soluble polymers is that they can induce inflammatory complications in certain ophthalmic treatment applications.

SUMMARY OF THE INVENTION

The present invention provides for novel pharmaceutical compositions of a polymer matrix and an active agent, and methods of treating or preventing a disease in a subject using the novel pharmaceutical compositions.

More particularly, certain embodiments set forth herein are generally directed to pharmaceutical compositions that include (1) a bioerodible water insoluble polymer matrix that includes a polyester polymer, wherein the polymer matrix has a melting point of less than 60° C.; and (2) an active agent dispersed within the polymer matrix, wherein the composition is formulated to controllably release the active agent for a pre-determined period of time to a target site.

The compositions of the present invention can include any additional component known to those of ordinary skill in the art. For example, the additional component may be an additional active agent, or a liquid component. In some embodiments, the composition includes a liquid component, which may be organic or aqueous. For example, in some embodiments, the composition includes up to 20% water miscible organic liquid. The water miscible organic liquid may or may not be miscible within the polymer matrix. In particular embodiments, the water miscible organic liquid is miscible within the polymer matrix.

The polyester polymer can be any polyester polymer known to those of ordinary skill in the art. For example, the polymer matrix may include a polyester polymer s selected from the group consisting of: poly(caprolactone)s; poly(ethylene glycol adipate)s; poly(propylene glycol adipate)s; poly(butylene glycol adipate)s; and blends and copolymers thereof. In particular embodiments, the polymer matrix comprises a poly(caprolactone) polymer, such as a poly(ϵ-caprolactone) polymer.

In certain embodiments, the polymer matrix includes a polyester polymer having the following structure:

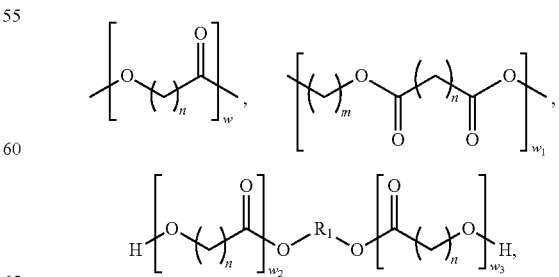

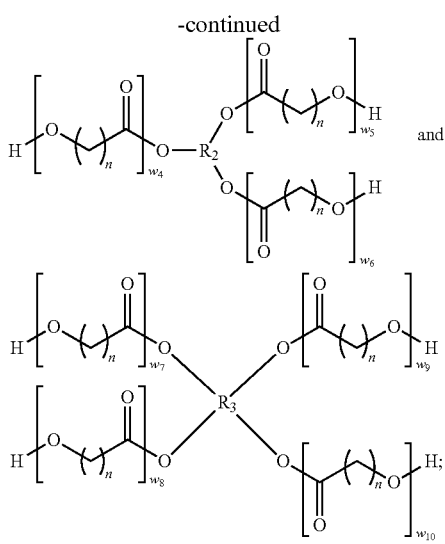

and wherein
$R_1$, $R_2$ and $R_3$ are selected from the group consisting of alkyl and alkoxyl diols, triols or tetraols of 2 to 8 carbon atoms;
w, $w_1$ are independently an integer from 4 to 12;
$w_2$, $w_3$ are independently an integer from 1 to 12;
$w_4$, $w_5$, $w_6$, $w_7$, $w_8$, $w_9$ and $w_{10}$ are independently an integer from 0 to 12;
n is an integer from 4 to 9; and
m is an integer from 2 to 8.

Non-limiting examples of the alkyl and alkoxyl diols, triols and tetraols of $R_1$, $R_2$ and $R_3$ include butanediol, hexanediol, neopentyl glycol, diethylene glycol, trimethylol propane and pentaerythritol. An example of a polyester polyol wherein $R_1$ is butanediol is as follows:

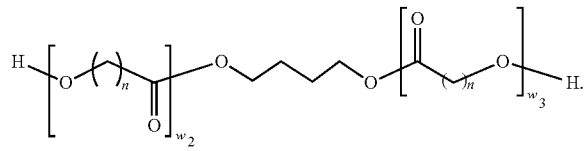

The polymer matrix may comprise polymers of any molecular weight. In particular embodiments, the polymers have an average molecular weight of 400 to 4000. Further, the polymer matrix may be of any viscosity. In particular embodiments, the viscosity of the polymer matrix is from 50 to 2000 cps at 55° C.

The polymer matrix may or may not be bioerodible. In particular embodiments, the polymer matrix or the composition is bioerodible.

In a preferred embodiment, the polymer matrix includes the polyester polymer 2-oxepanone, polymer with 2,2-bis (hydroxymethyl)-1,3-propanediol. This polymer is also known as epsilon-caprolactone polymer with pentaerythritol and has the chemical formula $(C_6H_{10}O_2)_x \cdot C_5H_{12}O_4$, where x is such that the polymer has an average molecular weight of about 1000. This polymer is commercially available from Solvay Chemicals, Inc. as CAPA® 4101.

In particular embodiments, one or more active agents are dispersed within the polymer matrix. Active agents include, but are not limited to, any component, compound, or small molecule that can be used to bring about a desired effect. For example, a desired effect can include the diagnosis, cure, mitigation, treatment, or prevention of a disease or condition.

In particular embodiments, the active agent is an ophthalmic drug. One of ordinary skill would be familiar with these agents, examples of which are set forth in the specification below. The active agent may or may not be in solution or suspension.

The ophthalmic drug may be an agent that is applied in the treatment or prevention of an eye disease. The eye disease can be any eye disease. In certain embodiments, the eye disease may be choroidal neovascularization (such as choroidal neovascularization due to age-related macular degeneration, dry (atrophic) age-related macular degeneration, or glaucoma. In some embodiments, the ophthalmic drug has anti-infective or anti-allergic properties.

In one embodiment, the ophthalmic drug is selected from the group consisting of known classes of ocular hypotensive drugs, such as carbonic anhydrase inhibitors, beta blockers, prostaglandins, bradykinin agonists, rho kinase inhibitors, C-type natriuretic peptides (CNP) receptor agonists, and guanylate cyclase activators.

The composition may be formulated to controllably release the active agent for a pre-determined period of time. The period of time can be of any length, such as one week, 4 weeks, 8 weeks, 6 months, or longer. Controlled release formulations are well-known to those of ordinary skill in the art, and are discussed elsewhere in this is specification. In particular embodiments, the composition is formulated to controllably release the active agent for at least four weeks to the target site.

The composition can be formulated in any manner known to those of ordinary skill in the art. For example, the composition may be formulated into an injectable paste or liquid.

Any method of administering the composition known to those of ordinary skill in the art is contemplated by the present invention. For example, in some embodiments, the pharmaceutical composition is formulated for topical application. Alternatively, the composition may be formulated for administration to a target site in the anterior segment or posterior segment of the eye. In particular embodiments, the composition is formulated for intravitreal injection.

The present invention is also generally directed to a method of treating a disease state in a subject that involves administering a therapeutically effective amount of any of the pharmaceutical compositions set forth above to a selected target site of the subject, wherein the active agent is controllably released to the target site for a predetermined period of time. The active agent can be any of those active agents set forth above, and elsewhere in this specification. In some embodiments, the active agent is controllably released into the target site for at least four weeks after administration.

The disease state can be any disease state. In particular embodiments, the disease state is an ophthalmic disease and the active agent is an ophthalmic drug.

The composition can be formulated in any method known to those of ordinary skill in the art. In particular embodiments, for example, the composition is formulated into an injectable paste or liquid. Further, any method of administration known to those of ordinary skill in the art is contemplated by the present methods. In certain particular embodiments, the composition is administered intravitreally.

In particular embodiments, the polyester polymers of the present invention can be selected from the group consisting of:

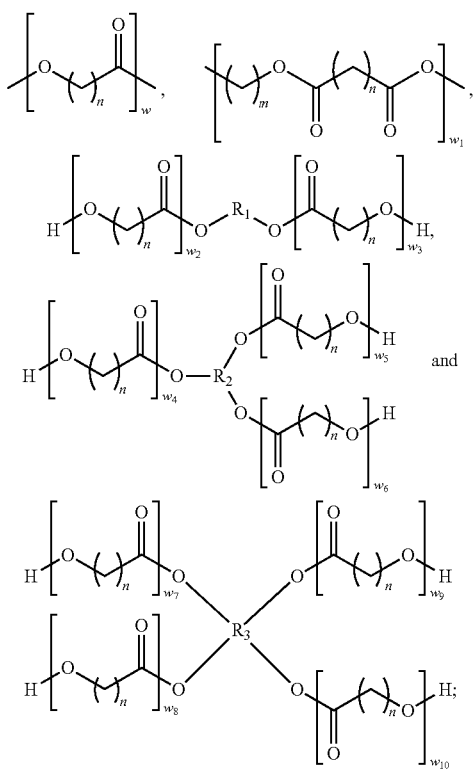

wherein
$R_1$, $R_2$ and $R_3$ are independently selected from the group consisting of alkyl and alkoxyl diols, triols and tetraols of 2 to 8 carbon atoms;
w, $w_1$ are independently an integer from 4 to 12;
$w_2$, $w_3$ are independently an integer from 1 to 12;
$w_4$, $w_5$, $w_6$, $w_7$, $w_8$, $w_9$ and $w_{10}$ are independently an integer from 0 to 12;
n is an integer from 4 to 9; and
m is an integer from 2 to 8.

Non-limiting examples of the alkyl and alkoxyl diols, triols and tetraols of $R_1$, $R_2$ and $R_3$ include butanediol, hexanediol, neopentyl glycol, diethylene glycol, trimethylol propane and pentaerythritol.

The present invention also generally pertains to methods of providing sustained release of an active agent to a selected target site in a subject that involves administering any of the pharmaceutical compositions of the present invention to the selected target site of the subject, wherein the active agent is released to the target site for a predetermined period of time. In some embodiments, for example, the active agent is sustainably released into the target site for at least four weeks after administration. In particular embodiments, the composition is formulated into an injectable paste or liquid.

Despite the lipophilic nature of the polymer matrix of the present invention, the ester group provides some polarity to the polymer system that results in increased solubility of certain drugs to the amounts needed for a practical drug delivery device. Furthermore, these polymers are miscible with biocompatible organic liquids such as propylene glycol and polyethylene glycols. This feature would allow a means to increase the solubility of the drug in the matrix and reduce the viscosity of the polymer. The reduction in viscosity results in lower force required to deliver the matrix through fine gauge needles or cannulas (collectively "syringes").

Any of those methods of administration known to those of ordinary skill in the art is contemplated by the present invention. Examples are discussed above and elsewhere in this specification. In particular embodiments, the composition is administered intravitreally.

The invention also pertains to kits that include a pharmaceutical composition of the present invention and a device for administering the pharmaceutical composition to a subject. Kits are discussed in greater detail in the specification below. The device for administering the pharmaceutical composition can be any device known to those of ordinary skill in the art. For example, the device may s include a syringe. It may also include a needle or cannula.

It is contemplated that any embodiment discussed in this specification can be implemented with respect to any method or composition of the invention, and vice versa. Furthermore, compositions of the invention can be used to achieve methods of the invention.

The term "bioerodible" includes the degradation, disassembly, or digestion of the compositions and/or polymers of the present invention by action of a biological environmental cue (e.g., acidity, temperature, or moisture of the target site, the existence of enzymes, proteins, or other molecules at the target site) or by action of the physical or chemical properties of the active agent dispersed within the matrix.

The term "matrix" includes the physical structure of the polymers of the present invention which retain the drug.

The term "subject" refers to either a human or non-human, such as primates, mammals, and vertebrates. In particular embodiments, the subject is a human.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of this specification and are included to further demonstrate certain non-limiting aspects of the present invention. The invention may be better understood by reference to one or more of these drawings in combination with the detailed description of specific embodiments presented in this specification.

DESCRIPTION OF ILLUSTRATIVE EMBODIMENTS

Figure 1:
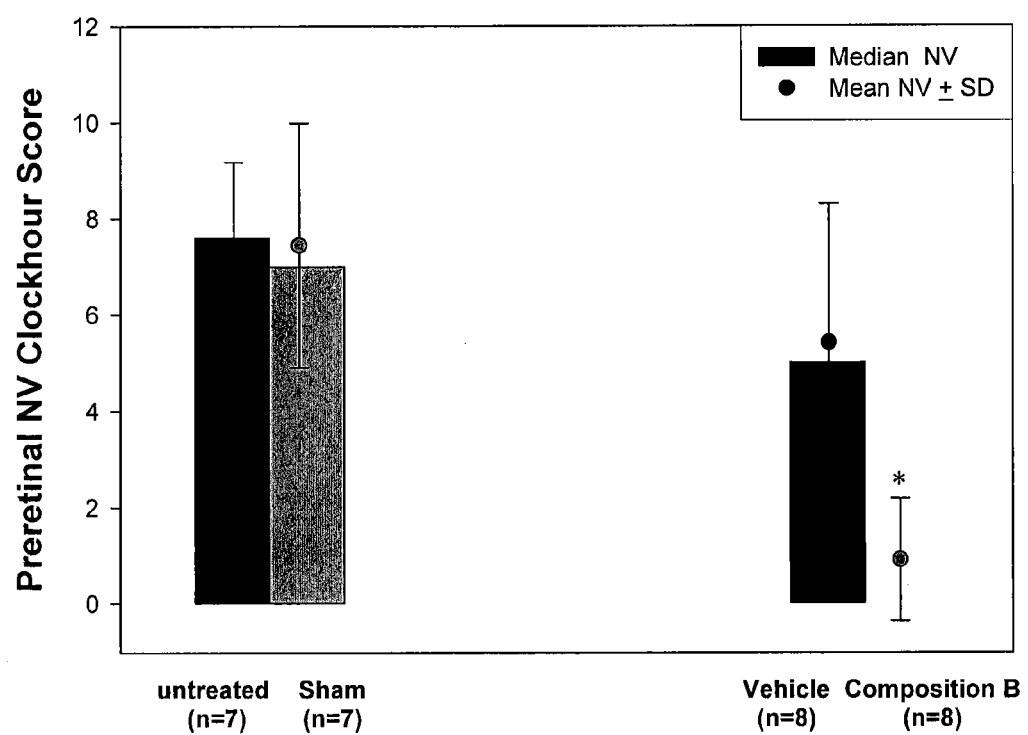
FIG. 1: Formulation study of RTKi candidate via single intravitreal injections in the rat OIR model.

Unless otherwise stated, all ingredient amounts presented as a percentage are in percent weight/weight terms (wt. %).

Current drug delivery treatment options are oftentimes ineffective due to the inefficient delivery of an active agent to a targeted site. For instance, injectable polymeric system which are liquid at room temperature and do not require solvents are POE polymers which are known to have relatively fast degradation times which can render them un-suitable as long-term controlled release drug delivery vehicles. As for water soluble polymers, it has been shown that the use of such polymers in drug delivery applications can cause inflammatory complications in certain ophthalmic treatment applications.

The water insoluble polymer matrix of the present invention provides a solution to the problems associated with current drug delivery options. For instance, the inventors have discovered unique injectable polymer matrices that allow convenient administration for the long-term sustained release of an active ingredient to a targeted site. This can allow the frequency of administrations to be reduced. The slow degradation of polymer network will result in slow release of the drug. Furthermore, since the degraded polymer produces acidic by-products, slow degradation will minimize any inflammation that results from acidic by-products (lower localized concentration of acids), which is common with bioerodable polymeric material. In certain instances, the sustained release of an active agent to a targeted site can extend over several weeks to months. The drug compound dispersed in polymer matrices can be injected to the specific target with little adverse effect to other organs. This allows for a wide range of diseases and conditions that currently affect today's society to be treated or prevented.

These and other aspects of the present invention are described in further detail in the following sections.

A. Water-Insoluble Polymer Matrix

Water insoluble polymer matrices of the present invention can be used to controllably release an active agent to a targeted site for a pre-determined period of time. In certain aspects, the polymer matrices are bioerodible and have a melting point of less than 60° C. The matrices can also have an average molecular weight of from 400 to 4000 and/or a viscosity of 100 to 2000 cps at 55° C.

The matrices of the present invention include polyester polymers. Non-limiting examples of polyester polymers that can be used include poly (ε-caprolactone)s, poly(alkylene glycol adipate)s, such as poly(ethylene glycol adipate), lo poly(propylene glycol adipate), poly(butylene glycol adipate), and blends and copolymers thereof. Poly(caprolactone) polymers are a preferred polyester polymer and are commercially available from Dow Chemical Company (located in Midland Mich.) and Solvay Chemicals, Inc. (located in Houston, Tex.) under the trade names TONE™ Polyol and CAPA™ Polyol, respectively.

In other non-limiting aspects, the polyester polymers of the present invention can be selected from the group consisting of:

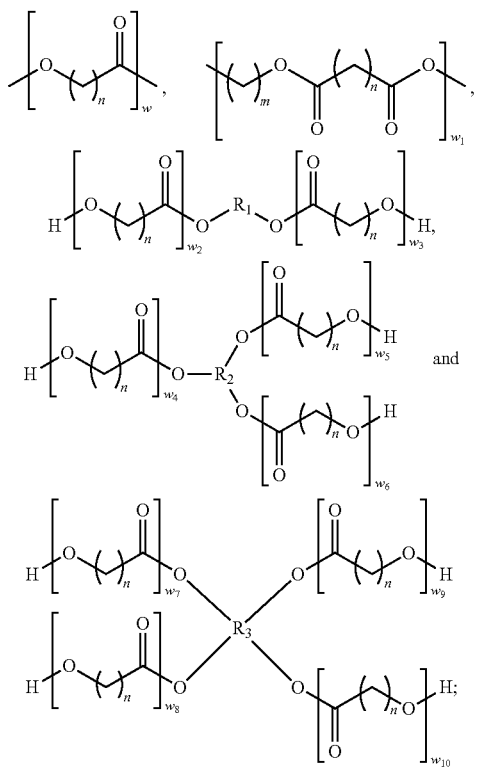

wherein
$R_1$, $R_2$ and $R_3$ are independently selected from the group consisting of alkyl and alkoxyl diols, triols and tetraols of 2 to 8 carbon atoms;
w, $w_1$ are independently an integer from 4 to 12;
$w_2$, $w_3$ are independently an integer from 1 to 12;
$w_4$, $w_5$, $w_6$, $w_7$, $w_8$, $w_9$ and $w_{10}$ are independently an integer from 0 to 12;
n is an integer from 4 to 9; and
m is an integer from 2 to 8.

Non-limiting examples of the alkyl and alkoxyl diols, triols and tetraols of $R_1$, $R_2$ and $R_3$ include butanediol, hexanediol, neopentyl glycol, diethylene glycol, trimethylol propane and pentaerythritol.

In non-limiting aspects, water-insoluble polymer matrices of the present invention can be prepared by dissolving or dispersing drug powder in polymer with mixing. In order to obtain a sterile drug product the following procedure can be used: if the drug to be tested is soluble in the polymer, drug powder is dispersed in the polymer with gentle heating up to 50° C. The drug-loaded polymer is then sterile filtered using a 0.22 μm membrane filter and filled in a pre-sterilized syringe. If the drug is not soluble in the polymer, the polymer is heated to about 50° C. and sterile filtered. The drug is sterilized by dry heat, gamma sterilization, ETO sterilization or other conventional method to sterilize drug compound that maintains the drug integrity. The drug powder and heated polymer are then mixed aseptically and then filled into pre-sterilized syringes. A paste polymeric matrix is preferred for this type of delivery, because the drug may not be settled from the matrix and insures the uniform consistency during storage. The paste can be opaque or transparent.

In certain aspects, the hydrophobic matrix can be formulated in such a way that the matrix does not undergo a physical change when administered (e.g., injection) to a subject. This typically includes compositions that are semi-solid paste so that the injection can be performed with a needle size no larger than about 22 gauge. An advantage of this type of formulation is that the active agents can be incorporated by mixing the active agents with the polymer matrix at room temperature and without the use of any solvents.

The compositions of the present invention generally comprise a polyester polymer in an amount of at least 50%, preferably at least 70%, and more preferably at least 80%. In some embodiments, the compositions comprise a polyester polymer in an amount of at least 85%. In other embodiments, the compositions of the present invention comprise a polyester polymer in an amount of at least 95%. In yet another embodiment, the compositions comprise a polyester polymer in an amount of at least 99%. In a preferred embodiment, the polyester polymer is CAPA-4101.

B. Active Agents

In certain non-limiting aspects, the water insoluble polymer matrices of the present invention can include an active agent. Active agents include, but are not limited to, any component, compound, or small molecule that can be used to bring about a desired effect. Non-limiting examples of desired effects of the present invention include diagnostic and therapeutic effects. For example, a desired effect can include the diagnosis, cure, mitigation, treatment, or prevention of a disease or condition. An active agent can also affect the structure or function of body part or organ in a subject.

In certain embodiments, the active agent is a hydrophobic drug. A hydrophobic active agent includes an agent that is sparingly soluble in aqueous media (e.g., not completely dissolved in the media at the concentration at which it is administered in an aqueous composition). Thus, depending upon the use and concentration, an active agent may be considered water-insoluble in one situation but not water-insoluble in another situation. However, a person of ordinary skill in the art would recognize that the active agent does not need to be a hydrophobic drug in the context of the present invention.

1. Ophthalmic Drugs

A preferred class of active agents includes ophthalmic drugs. Non-limiting examples include: anti-glaucoma agents; anti-angiogenesis agents; anti-infective agents; anti-inflammatory agents; growth factors; immunosuppressant agents; and anti-allergic agents. Anti-glaucoma agents include beta-blockers, such as timolol, betaxolol, levobetaxolol, and carteolol; miotics, such as pilocarpine; carbonic anhydrase inhibitors, such as brinzolamide and dorzolamide; prostaglandins, such as travoprost, bimatoprost, and latanoprost; seretonergics; muscarinics; dopaminergic agonists; and adrenergic agonists, such as apraclonidine and brimonidine. Anti-angiogenesis agents include anecortave acetate (RE-TAANE™, Alcon™ Laboratories, Inc. of Fort Worth, Tex.) and receptor tyrosine kinase inhibitors. Anti-infective agents include quinolones, such as ciprofloxacin, moxifloxacin, and gatifloxacin, and aminoglycosides, such as tobramycin and gentamicin. Anti-inflammatory agents include non-steroidal and steroidal anti-inflammatory agents, such as suprofen, diclofenac, ketorolac, nepafenac, rimexolone, and tetrahydrocortisol. Growth factors include EGF. Anti-allergic agents include olopatadine and epinastine. The ophthalmic drug may be present in the form of a pharmaceutically acceptable salt, such as timolol maleate, brimonidine tartrate or sodium diclofenac.

In one embodiment, the ophthalmic drug is selected from the group consisting of known classes of ocular hypotensive drugs, such as carbonic anhydrase inhibitors, beta-blockers, prostaglandins, bradykinin agonists, rho-kinase inhibitors, CNP receptor agonists, and guanylate cyclase activators.

2. Additional Active Agents

Although ophthalmic drugs are a preferred active agent of the present invention, the inventors contemplate that other active agents can be used. The following includes non-limiting examples of these other active agents, and it should be recognized that some these active agents may be generic to or identical to the ophthalmic drugs identified above. A reason for this is that some ophthalmic drugs can be used to treat or prevent other diseases or conditions. Further, it is also possible that some of the following active agents that are not identified in the above section can be used to treat ophthalmic diseases or conditions.

Active agents such as nucleic acids, proteins and peptides, hormones and steroids, chemotherapeutics, NSAIDs, vaccine components, analgesics, antibiotics, anti-depressants, etc. are contemplated as being useful in the context of the present invention. Non-limiting examples of nucleic acids that can be used include DNA, cDNA, RNA, iRNA, siRNA, anti-sense nucleic acid, peptide-nucleic acids, oligonucleotides, or nucleic acids that are modified to improve stability (e.g., phosphorothioates, aminophosphonates or methylphosphonates).

Proteins and peptides that can be used with the present invention include but are not limited to human growth hormone, bovine growth hormone, vascular endothelial growth factor, fibroblast growth factors, bone morphogenic protein, tumor necrosis factors, erythropoietin, thrombopoietin, tissue plasminogen activator and derivatives, insulin, monoclonal antibodies (e.g., anti-human epidermal growth factor receptor 2 (Herceptin), anti-CD20 (Rituximab), anti-CD 18, anti-vascular endothelial growth factor, anti-IgE, anti-CD 11a) and their derivatives, single-chain antibody fragments, human deoxyribonuclease I (domase alfa, Pulmozyme), type-1 interferon, granulocyte colony-stimulating factor, leuteinizing hormone releasing hormone inhibitor peptides, leuprolide acetate, endostatin, angiostatin, porcine factor VIII clotting factor, interferon alfacon-1, and pancrelipase (pancreatic enzymes).

Non-limiting examples of hormones and steroids that can be used include norethindrone acetate, ethinyl estradiol, progesterone, estrogen, testosterone, prednisone and the like. Other examples of steroids include glucocorticoids, progestins, mineralocorticoids, and corticosteroids. Exemplary corticosteroids include cortisone, hydrocortisone, prednisone, prednisolone, methylprednisone, triamcinolone, fluoromethalone, dexamethasone, medrysone, betamethasone, loteprednol, fluocinolone, flumethasone, or mometasone. Other examples of steroids include androgens, such as testosterone, methyltestosterone, or danazol. Often steroids are administered as ester, acetal, or ketal prodrugs, many of which are water-insoluble. These prodrugs are also considered to be steroids in the context of the present invention.

Chemotherapeutics that can be used include but are not limited to taxol (Paclitaxel), vinblastine, cisplatin, carboplatin, tamoxifen and the like.

Non-limiting examples of NSAIDs include piroxicam, aspirin, salsalate (Amigesic), diflunisal (Dolobid), ibuprofen (Motrin), ketoprofen (Orudis), nabumetone (Relafen), piroxicam (Feldene), naproxen (Aleve, Naprosyn), diclofenac (Voltaren), indomethacin (Indocin), sulindac (Clinoril), tolmetin (Tolectin), etodolac (Lodine), ketorolac (Toradol), oxaprozin (Daypro), and celecoxib (Celebrex).

Vaccine components that can be used include but are not limited to Hepatitis B, polio, measles, mumps, rubella, HIV, hepatitis A (e.g., Havrix), tuberculosis, etc.

Non-limiting examples of analgesics include but are not limited to aspirin, acetaminophen, ibuprofen, naproxen sodium and the like.

Antibiotics include but are not limited to amoxicillin, penicillin, sulfa drugs, erythromycin, streptomycin, tetracycline, clarithromycin, tobramycin, ciprofloxacin, terconazole, azithromycin and the like.

Anti-depressants include but are not limited to Zoloft, fluoxetine (Prozac), paroxetine (Paxil), citalopram, venlafaxine, fluvoxamine maleate, imipramine hydrochloride, lithium, nefazodone and the like.

Non-limiting examples of additional active ingredients can be found in Physician's Desk Reference 2000, 54th Edition, ISBN: 1563633302, AHFS 99 Drug Information, and Amer. Soc. of Health System, ISBN: 1879907917, which are incorporated by reference.

C. Treatment and Prevention of Diseases and Conditions

A "disease" or "health-related condition" can be any pathological condition of a body part, organ, or system of a subject. In certain instances, the condition can be the result of any cause, including for example, infection, genetic defect, and/or environmental stress. The cause may or may not be known.

It is contemplated that the pharmaceutical compositions of the present invention can be used to treat or prevent a variety of diseases or conditions. Non-limiting examples of such diseases and conditions include ophthalmic diseases or conditions, pulmonary associated diseases or conditions (e.g., common cold, flu, cystic fibrosis, emphysema, asthma, tuberculosis, severe acute respiratory syndrome, pneumonia, lung cancer, etc.), circulatory diseases or conditions, muscular diseases or conditions, bone diseases or conditions, infections, cancers, heart diseases(s), etc.

In certain preferred embodiments, the disease or condition to be treated is an ophthalmic disease or condition. Non-limiting examples include dry eyes, meibomitis, glaucoma, conjunctivitis, iritis, ocular neovascularization, macular edema, ocular neovascularization, diabetic retinopathy, age-related macular degeneration, or any condition associated with ocular inflammation.

The subject can be a subject who is known or suspected of being free of a particular disease or health-related condition at the time the relevant preventive agent is administered. The subject, for example, can be a subject with no known disease or health-related condition (i.e., a healthy subject). In some embodiments, the subject is a subject at risk of developing a particular disease or health-related condition. For example, the subject may have a history of allergic conjunctivitis that has been treated in the past, who is at risk of developing a recurrence of the allergic conjunctivitis.

In additional embodiments of the invention, methods include identifying a patient in need of treatment. A patient may be identified, for example, based on taking a patient history, or based on findings on clinical examination In order to increase the effectiveness of a treatment with the compositions of the present invention, it may be desirable to combine these compositions with other therapies effective in the treatment of a particular disease or condition. The compositions of the present invention, for example, can precede or follow the other agent treatment by intervals ranging from minutes to weeks. It is contemplated that one may administer both modalities within about 12-24 h of each other and, more preferably, within about 6-12 h of each other. In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, or more) lapse between the respective administrations.

Various combinations may be employed where "A" represents compositions of the present invention and "B" represents the secondary agent or therapy:

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | | B/B/A/B | A/A/B/B | | A/B/A/B | A/B/B/A | B/B/A/A |
| B/A/B/A | | B/A/A/B | A/A/A/B | | B/A/A/A | A/B/A/A | A/A/B/A. |

D. Pharmaceutical Compositions and Routes of Administration

One embodiment of this invention includes methods of treating, preventing, or diagnosing a particular disease or condition by administering a pharmaceutical composition that includes the water insoluble polymer matrix and/or active agent of the present invention to a subject. The administration can be local or systemic. An effective amount of a pharmaceutical composition, generally, is defined as that amount sufficient to ameliorate, reduce, minimize or limit the extent of the disease or condition. More rigorous definitions may apply, including elimination, eradication or cure of the disease or condition.

1. Pharmaceutical Compositions

Pharmaceutical compositions of the present invention can include a water insoluble polymer matrix. In certain aspects, an active agent is dispersed throughout the matrix. The phrases "pharmaceutical or pharmacologically acceptable" can include but are not limited to molecular entities and compositions that do not produce an adverse, allergic or other untoward reaction when administered to a subject, such as, for example, a human. The preparation of a pharmaceutical composition is generally known to those of skill in the art. Remington's Pharmaceutical Sciences, 18th Ed. Mack Printing Company, 1990. Moreover, for animal (e.g., human) administration, it is preferred that the preparations meet sterility, pyrogenicity, general safety and purity standards as required by FDA Office of Biological Standards.

"Therapeutically effective amounts" are those amounts effective to produce beneficial results in the recipient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

"Pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, lo determine the concentration of active ingredient(s) in a composition and appropriate dose(s) for the individual subject.

In certain non-limiting embodiments, pharmaceutical compositions may comprise, for example, at least about 0.001%, by weight, of an active ingredient. In other embodiments, the active ingredient may comprise from about 0.002% to about is 50% of the weight of the compositions, and any range derivable therein. In still other embodiments, the active ingredient may comprise from about 0.5% to about 5% of the compositions. In further embodiments, the concentration of active agent is about 5% to about 30%. In still further embodiments, the concentration of active agent in the device is about 10% to about 20% by weight.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

The compositions may additionally contain up to 50% water miscible organic liquids that are miscible in above polyester polymers. In some embodiments, the amount of water miscible organic liquid is 20% or less. Examples of miscible organic liquids are propylene glycol and low molecular weight polyethylene glycols such as PEG-400 and PEG-600. These liquids are also water soluble and thus will modify the drug release profile and erosion rate of polyester polymer matrix in-vivo. Additionally, these organic liquids reduce the viscosity of the drug loaded matrix.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g. , triglycerides, vegetable oils, liposomes) and combinations thereof. In many cases, it will be preferable to include isotonic agents, such as, for example, sugars, sodium chloride or combinations thereof. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal composite ions, troches, elixirs, suspensions, syrups, wafers, or combinations thereof. Oral compositions may be incorporated directly with the food of the diet. Preferred carriers for oral administration comprise inert diluents, edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

The composition should be stable under the conditions of manufacture and storage, and preserved against the contaminating action of microorganisms, such as bacteria and fungi. A person of ordinary skill in the art would understand that the concentrations can vary depending on the addition, substitution, and/or subtraction of ingredients in a given composition.

2. Controlled or Sustained Release Pharmaceutical Compositions

Pharmaceutical compositions of the present invention can be formulated to controllably or sustainably release the active ingredient(s) to a target site. The phrases "controlled release", "sustained release", and similar terms and phrases describe a mode of active agent delivery that occurs when the active agent is released from the delivery vehicle at an ascertainable and controllable rate over a period of time, rather than dispersed immediately upon application or injection. Controlled or sustained release may extend for hours, days, months, or years and can vary as a function of numerous factors. For instance, the rate of release can depend on the type of the excipient(s) selected and/or the concentration of the excipient(s) in the composition. Another determinant of the rate of release is the rate of hydrolysis of the linkages between and within the monomer units of the water insoluble polymer matrix of the present invention. The rate of hydrolysis can be controlled by the concentration of the polymers and/or by the number of hydrolysable bonds within a given polymer. Other factors determining the rate of release of an active agent from the present pharmaceutical compositions include the acidity, temperature, or moisture of the target site, the existence of enzymes, proteins, or other molecules at the target site, or the physical or chemical properties of the active agent dispersed within the matrix.

3. Routes of Administration

Compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, intrathecally, topically, intratumorally, intramuscularly, intraperitoneally, subcutaneously, subconjunctival, intravesicularlly, mucosally, intrapericardially, intraumbilically, intraocularly, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

In certain preferred embodiments, the composition is administered topically or locally to the eye of a subject. It is contemplated that all local routes to the eye may be used including topical, subconjunctival, periocular, retrobulbar, subtenon, intracameral, intravitreal, intraocular, subretinal, posterior juxtascleral, and suprachoroidal administration. In particular embodiments the formulations are suitable for application to mammalian eyes.

In an especially preferred embodiment, the composition is a non-aqueous liquid composition that comprises a poly(caprolactone) polymer and an ophthalmic drug that is soluble in the poly(caprolactone) polymer. Such a composition has the advantages that it can be prepared, sterilized (by sterile filtration), stored, shipped, and administered as a liquid. For example, such a liquid composition may be packaged in a pre-loaded syringe and injected (e.g., through a 22-gauge needle or smaller, especially a 27- or 30-gauge needle) into the vitreous or other parts of the eye.

E. Source of Ingredients

The ingredients and components of the compositions of the present invention that are described in the claims and specification can be obtained by any means known to a person of ordinary skill in the art. In a non-limiting embodiment, for example, these ingredients can be isolated by obtaining the source of such compounds, agents, and active ingredients. In many instances, the ingredients are commercially available.

F. Modifications and Derivatives

Modifications or derivatives of ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. Such derivatives may have the addition, removal, or substitution of one or more chemical moieties on the parent molecule. Non limiting examples of the types modifications that can be made to the compounds and structures disclosed throughout this document include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, hetero atoms such as N, S, or O can be substituted into the structure instead of a carbon atom.

G. Equivalents

Known and unknown equivalents to the ingredients discussed throughout this specification can be used with the compositions and methods of the present invention. In some instances, for example, equivalents can be used as substitutes. The equivalents can also be used to add to the methods and compositions of the present invention. A person of ordinary skill in the art would be able to recognize and identify acceptable known and unknown equivalents to the ingredients without undue experimentation.

H. Additional Components that Can be Used in the Compositions of the Present Invention Compositions of the present invention can include other agents, compounds, and excipients such as emulsions. Non-limiting examples include surfactants, preservatives, stabilizers, structuring agents, thickeners, and lipids.

1. Surfactants

The compositions of the present invention can also comprise one or more surfactants. Surfactants can reduce the in interfacial tension between phases and improve the formulation and stability of a formulation. The surfactants can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, cetyl phosphate, potassium cetyl phosphate, diethanolamine cetyl phosphate, polysorbate 20, polysorbate 60, polysorbate 80, glyceryl stearate, PEG-100 stearate, tyloxapol, and mixtures thereof.

2. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), chlorobutanol, phenol, sorbic acid, thimerosal or combinations thereof.

3. Stabilizers

Non-limiting examples of preservatives that can be used in the context of the present invention include chelating agents and antioxidants. Examples of chelating agents include, but are not limited to any natural or synthetic chemical which has the ability to bind divalent cationic metals such as $Ca^{++}$, $Mn^{++}$, or $Mg^{++}$. In preferred aspects, the chelating agent is selected from EDTA, disodium EDTA, EGTA, citric acid, and dicarboxylic acids.

Examples of antioxidants include, but are not limited to, acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

4. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

5. Thickening Agents (Including Thickeners and Gelling Agents)

In certain embodiments, the compositions of the present invention can include one or more thickening agents. Non-limiting examples include carboxylic acid polymers, crosslinked polyacrylate polymers, polyacrylamide polymers, polysaccharides, and gums.

Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80. Examples of commercially available carboxylic acid polymers include carbomers, which are homopolymers of acrylic acid crosslinked with allyl ethers of sucrose or pentaerytritol (e.g., Carbopol™ 900 series from B. F. Goodrich.

Examples of crosslinked polyacrylate polymers include cationic and nonionic polymers. Examples are described in U.S. Pat. Nos. 5,100,660; 4,849,484; 4,835,206; 4,628,078; 4,599,379).

Examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

6. Lipids

Non-limiting examples of lipids that can be used in the compositions of the present invention include neutral lipids, which exist either in an uncharged or neutral zwitterionic form at physiological pH. Examples include phospholipids, such as phosphatidylcholine, sphingomyelin, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine and dilinoleoylphosphatidylcholine.

The lipid may be a cationic lipid, or a lipid that carries a net positive charge at physiological pH. Such cationic lipids include, but are not limited to, N,N-dioleyl-N,N -dimethylammonium chloride ("DODAC"); N-(2,3-dioleyloxy)propyl-N,N-N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N-(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethyl -ammonium trifluoracetate ("DOSPA"), dioctadecylamidoglycyl carboxyspermine ("DOGS"), 1,2-dileoyl-sn-3-phosphoethanolamine ("DOPE"); N-(1,2-dimyristyloxyprop-3-yl)-N,N-dimethyl-N-hydroxyethyl ammonium bromide ("DMRIE"); stearylamine; dimethyl-dioctadecylammonium bromide; 3B-[N',N'-dimethylaminoethane]-carbamol, stearylamine, DC-Cholesterol, dimethyldioctadecylammonium bromide, or 3B-[N',N'-dimethylaminoethane]-carbamol.

I. Kits

In further embodiments of the invention, there is provided a kit. The kit can include, in non-limiting aspects, the pharmaceutical compositions of the present invention and other ingredients described in the claims and specification. Containers of the kits can include a bottle, dispenser, package, compartment, syringe, needle (e.g., gauge of 7, 8, 9, 10, 15, 20, 25, 30, 31, 32, 33, etc.) or other types of containers. The container can include indicia on its surface. The indicia, for example, can be a word, a phrase, an abbreviation, a picture, or a symbol.

The containers can dispense a pre-determined amount of the component (e.g. compositions of the present invention). The composition can be dispensed in a spray, an aerosol, or in a liquid form or semi-solid form. The containers can have spray, pump, or squeeze mechanisms. In certain aspects, the kit can include a syringe for Is administering the compositions of the present invention.

Where there is more than one component in the kit (they may be packaged together), the kit also will generally contain a second, third or other additional containers into which the additional components may be separately placed. The kits of the present invention also can include a container housing the components in close confinement for commercial sale. Such containers may include injection or blow-molded plastic containers into which the desired bottles, dispensers, or packages are retained.

A kit can also include instructions for employing the kit components as well the use of any other compositions, compounds, agents, active ingredients, or objects not included in the kit. Instructions may include variations that can be implemented. The instructions can include an explanation of how to apply, use, and maintain the products or compositions, for example.

EXAMPLES

The following examples are included to demonstrate certain non-limiting aspects of the invention. It should be appreciated by those of skill in the art that the techniques disclosed in the examples represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Preparation of a Non-Limiting Embodiment of a Water-Insoluble Polymer Matrix Water-insoluble polymer matrices of the present invention can be prepared by dissolving or dispersing drug powder in polymer with mixing. In order to obtain a sterile drug product the following procedure can be used: if the drug to be tested is soluble in the polymer, drug powder is dispersed in polymer system with gentle heating up to 50° C. The drug loaded polymer is then sterile filtered using 0.22 mm membrane filter and filled in pre-sterilized syringe. If the drug is not soluble in the polymer, the polymer is heated to about 50° C. and sterile filtered. The drug is sterilized by dry heat, gamma sterilization, ETO sterilization or other conventional 1s method to sterilize drug compound that maintains the drug integrity. The drug powder and heated polymer are then mixed aseptically and then filled into pre-sterilized syringes. A paste polymeric matrix is preferred for this type of delivery, since the drug will not be settled from the matrix and insures the uniform consistency upon storage.

Example 2

Characteristics of Non-limiting Water-Insoluble Polymer Matrices

The following Table 1 includes non-limiting examples of water-insoluble polymer matrices that can be used in the context of the present invention. These polymers are based on polycaprolactone. The physical properties of these polymers and their commercial availability are listed in Table 1:

TABLE 1

|  | PCL-900 | Tone 310 | CAPA 3091 | CAPA 2101A | Tone 2221 | CAPA PL-1000 | Tone 1231 | CAPA 4101 |
|---|---|---|---|---|---|---|---|---|
| Supplier | Sigma | Dow | Solvay | Solvay | Dow | Solvay | Dow | Solvay |
| polyol | TMP | TMP | TMP | 2-NPG | 2-NPG | none | BDO | 4-PENA |
| MW | 900 | 900 | 900 | 1000 | 1000 | 1000 | 1250 | 1000 |
| Mp/° C. | Softening point 30° C. | 27-32 | 0-10 | 30-40 | 15-40 | 10-20 | 20-45 | 10-20 |
| Physical form at RT | paste | paste | clear liquid | paste | paste | paste | wax | clear liquid |
| Viscosity/cps | 272 @ 55 C. | 270 @ 55 C. | 165 @ 60 C. | 150 @ 60 C. | 180 @ 55 C. | 150 @ 60 C. | 200 @ 55 C. | 260 @ 60 C. |

PCL-900 = Tone 310 = CAPA 3091 = Polycaprolactone triol with TMP as triol

CAPA 2101A = Tone 2221 = Polycaprolactone diol with NPG as the diol

CAPA PL-1000 = Polycaprolactone with mw of 1000 with no polyols

Tone 1232 = Polycaprolactone diol with butane diol (BDO) as the diol

TMP = Trimethylol propane

NPG = Neopantyl glycol

BDO = Butane diol

PENTA = Pentaerythritol

Volatile impurities were evaluated gravimetrically following 5 hours in vacuum oven at 80° C.

The erosion rates of the polymers in Table 1 were determined by monitoring weight loss after storing in phosphate buffered saline (PBS) at pH 7.4. The weight loss was determined after exposing the polymer to PBS saline at 37° C. The saline was removed and vial was dried and weight loss was determined. The rate of erosion after 2 weeks and 4 weeks are shown below in Table 2. The pH of the saline solution (originally at pH 7.4) is also reported below.

TABLE 2

|  | PCL-900 | Tone 310 | CAPA 3901 | CAPA 2101A | Tone 2221 | CAPA PL-1000 | Tone 1231 | CAPA 4101 |
|---|---|---|---|---|---|---|---|---|
| Volatile Impurities % (5 hours/ 80° C.) | 3.9 | 2.8 | 0.3 | 2.0 | 1.1 | 3.5 | 3.4 | 1.2 |

| Erosion | %* Wt Loss | pH saline | % Wt Loss | pH saline | % Wt Loss | pH saline | %*Wt Loss | pH saline | % Wt Loss | pH saline | % Wt Loss | pH saline | % Wt Loss | pH saline | %***Wt Loss | pH saline |
|---|---|---|---|---|---|---|---|---|---|---|---|---|---|---|---|---|
| @ 2 week | 5 | NT | 9.8 | 7.01 | 7.7 | 7.24 | 4.3 | 7.23 | 6.6 | 7.20 | 8.7 | 7.21 | 2.9 | 7.10 | 9.7 | 7.24 |
| @ 4 week | 4.5 | 6.87 | 8.9 | 6.87 | 8.0 | 7.12 | 4.0 | 7.23 | 3.0 | 7.20 | 3.8 | 7.21 | 3.5 | 7.10 | 8.0 | 7.24 |

*1 g polymer in 10 ml PBS at pH 7.4 @ 37° C.
**1 g polymer in 20 ml PBS at pH 7.4 @ 37° C.
***0.5 g polymer in 20 ml PBS at pH 7.4 @ 37° C.
NT = Not Tested Example 2

Non-limiting Example of a Composition

A composition of a receptor tyrosine kinase inhibitor (RTKi) candidate in a tetra-functional terminated polyol of polycaprolactone (CAPA 4101) with a molecular weight of 1000 was prepared in the context of the present invention. The drug was found to be soluble in CAPA 4101 which is liquid at room temperature above 1% w/w as illustrated in Tables 3 and 4.

TABLE 3

|  | A | B |
|---|---|---|
| RTKi | 1% | 1% |
| Propylene glycol | — | 5% |
| CAPA 4101 | 99% | 94% |

The above compositions were prepared by dispersing the liquids and adding the drug solids to the liquids and allowing the drug to dissolve in the polymer with mixing. The drug composition is then sterile filtered using 0.22 µm filter and filled in pre-sterilized syringe. Both compositions were clear.

The thermal stability of the drug in the above compositions were determined and are set forth in Table 4 below. The results show reasonable stability at 50° C., supporting a shelf life stability of over 1 year at room temperature.

TABLE 4

| Formulation ID | Initial % of Label | 50° C./9 days % of Label (% of Initial) | 50° C./ 38 days % of Label (% of Initial) | 50° C./ 109 days % of Label (% of Initial) |
|---|---|---|---|---|
| 1% RTKi in CAPA with 5% PG (Composition B) | 98.0 | 97.0 (99.0) | 91.7 (93.6) | 80.3 (81.9) |
| 1% RTKi in CAPA (Composition A) | 99.4 | 98.6 (99.2) | 93.6 (94.2) | 84.7 (85.2) |

Example 3

Efficacy of Composition

Screening of a composition B of Table 3 (Example 2 above) against posterior segment angiogenesis in the Rat Model of Oxygen-induced Retinopathy (OIR) was carried out.

Pregnant Sprague-Dawley rats were received at 14 days gestation and subsequently gave birth on day 22±1 of gestation. Immediately following parturition, pups were pooled and randomized into separate litters (n=17 pups/litter), placed into separate shoebox cages inside oxygen delivery chamber, and subjected to the Double 50 oxygen-exposure profile from Day 0-14 postpartum. Litters were then placed into room air from day 14/0 through day 14/6 (days 14-20 postpartum). Additionally on day 14/0, each pup was randomly assigned to the treatment groups and control.

At day 14/6 (20 days postpartum), all animals were euthanized. Immediately following euthanasia, retinas from all rat pups were harvested, fixed in 10% neutral buffered formalin for 24 hours, subjected to ADPase staining, and fixed onto slides as whole mounts. As the retinas were processed, the success of the vascular staining was confirmed by observation through a dissection scope. A Nikon Eclipse E800® microscope and a Photometrics CoolSNAP fxdigital camera were used to acquire images from each retinal flat mount that was adequately prepared. Computerized image analysis using Metamorph® software was used to obtain a NV clockhour score from each readable sample. Each clockhour out of 12 total per retina was assessed for the presence or absence of preretinal NV. Statistical comparisons using median scores for NV clockhours from each treatment group were utilized in nonparametric analyses. Because the pups were randomly assigned and no difference was observed between the NV scores of control pups from all litters, the NV scores were combined for all treatment groups. P≤0.05 was considered statistically significant.

FIG. 1 shows the results. The tested RTKi composition (Composition B) showed good efficacy with no adverse retinal effects.

Example 4

Ocular safety in Rabbits

A 2 week ocular acceptability of the polymer marix of last example was evaluated by intravitreal injection of 100 ml of test article or BSS (Alcon Laboratories, Inc.) Irrigation solution (as control) in the right eye. 3 white New Zealand F1 Pigmented Rabbits were used fer arm in the study. All injections were through 27 or 30 guage syringe needle. During the observation period, general health observation, body weight, slit lamp biomicroscopy, indirect observations, corneal thickness(pachymetry) and intraocular pressure were assessed. Animals were euthanized after a 14-day observation period. Eyes and Ocular adnexa were examined by microscopy. No significant finding related to general health observation, body weight or ocular observations including slit lamp biomicroscopy, indirect evaluations, corneal thickness or intraocular pressures were observed. No gross lesions were observed at necropsy. No test article-related changes were observed in the ocular adnexa in any of the treated rabbits.

Example 5

Erosion Study

Figure 2:
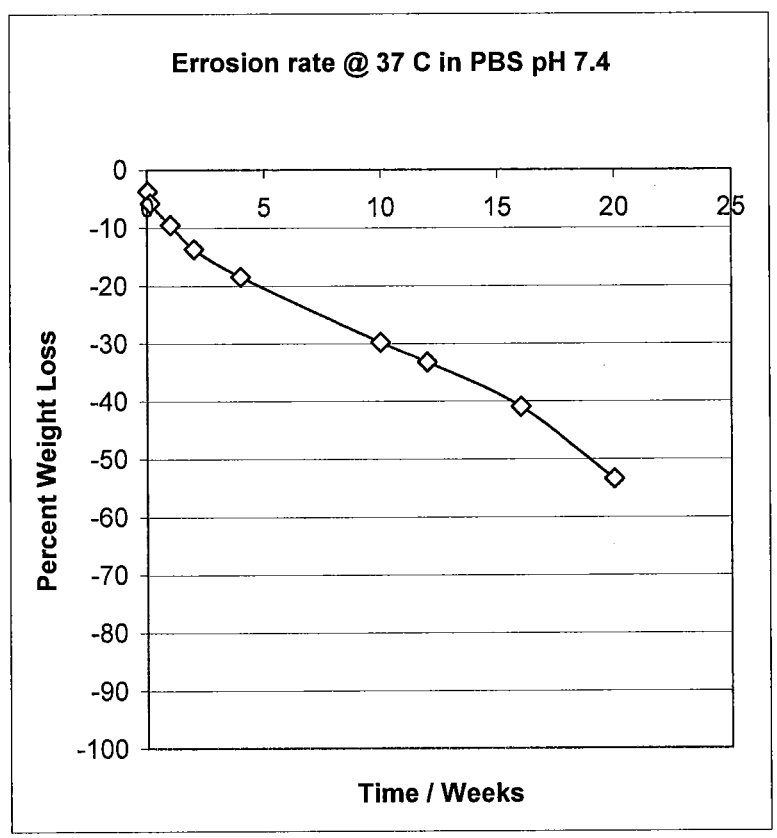
FIG. 2: Erosion rate study of CAPA-4101 polymer.

The erosion rate of CAPA-4101 was evaluated gravimetrically by preparing replicate samples each containing 0.5 g of polymer in 20 ml of saline solution. The polymer was dried and weighed at a given time pull (n=2 for each time point) and the weight loss is reported in FIG. 2. The results, as shown in FIG. 2, indicated slow erosion of the polymer over several months.

* * *

All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth in this specification, are specifically incorporated by reference.

U.S. Pat. No. 2,798,053
U.S. Pat. No. 3,755,560
U.S. Pat. No. 4,079,038
U.S. Pat. No. 4,093,709
U.S. Pat. No. 4,131,648
U.S. Pat. No. 4,138,344
U.S. Pat. No. 4,180,646
U.S. Pat. No. 4,304,767
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,648,506
U.S. Pat. No. 6,995,186
U.S. Patent Publn. 2003/0055102
U.S. Patent Publn. 2005/0158387
U.S. Patent Publn. 2006/0009498
AHFS 99 Drug Information
Amer. Soc. Of Health System, ISBN: 1879907917
CTFA International Cosmetic Ingredient Dictionary, Fourth edition, 1991, pp. 12 and 80.
McCutcheon's, Detergents and Emulsifiers, North American Edition (1986).
Physician's Desk Reference, 54$^{th}$ Ed., ISBN: 1563633302, 2000.
Remington's Pharmaceutical Sciences, 18$^{th}$ Ed. Mack Printing Company, pp. 1289-1329, 1990.

What is claimed is:

1. A pharmaceutical composition comprising:
   (a) a bioerodible water insoluble polymer matrix comprising a polyester polymer, wherein the polymer matrix has a melting point of less than 60° C. and wherein the polyester polymer has an average molecular weight of 400 to 4000 and wherein the polyester polymer is at least 80 wt % of the composition; and
   (b) an active agent dispersed within the polymer matrix;
   wherein the active agent is an ophthalmic drug and wherein the viscosity of the composition is from 100 to 2000 cps at 55° C. and wherein the composition is formulated to controllably release the active agent within a vitreous of an eye for a pre-determined period of time and wherein the composition is a liquid or paste that can be injected through a needle no larger than 22 gauge into the vitreous without requiring a physical change of the composition.

2. The pharmaceutical composition of claim 1, wherein the composition comprises a water miscible liquid incorporated in the matrix and wherein the concentration of the water miscible liquid is up to 50% (w/w).

3. The pharmaceutical composition of claim 2, wherein the water miscible organic liquid is miscible within the polymer matrix.

4. The pharmaceutical composition of claim 1, wherein the polymer matrix comprises a polymer selected from the group consisting of: poly(∊-caprolactone)s; poly(ethylene glycol adipate)s; poly(propylene glycol adipate)s; poly(butylene glycol adipate)s; and blends and copolymers thereof.

5. The pharmaceutical composition of claim 4, wherein the polymer matrix comprises a poly(∊-caprolactone) polymer.

6. The pharmaceutical composition of claim 1, wherein the polymer matrix comprises a polyester polymer selected from the group consisting of:

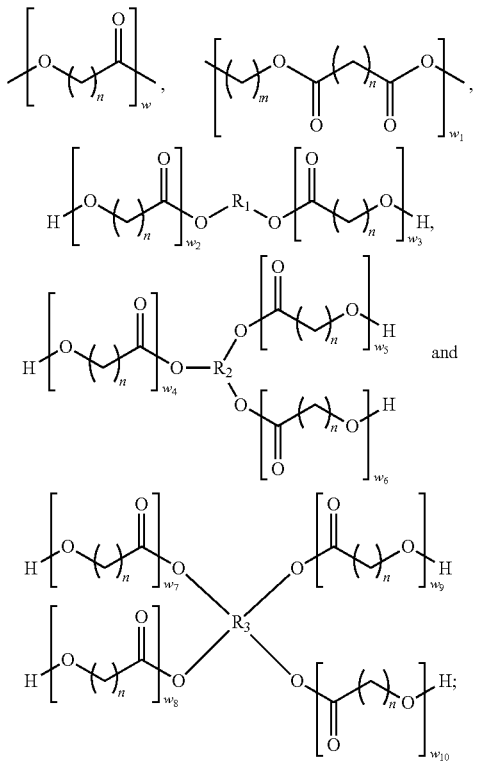

wherein $R_1$, $R_2$ and $R_3$ are independently selected from the group consisting of alkyl and alkoxyl diols, triols and tetraols of 2 to 8 carbon atoms;

$w$, $w_1$ are independently an integer from 4 to 12;

$w_2$, $w_3$ are independently an integer from 1 to 12;

$w_4$, $w_5$, $w_6$, $w_7$, $w_8$, $w_9$ and $w_{10}$ are independently an integer from 0 to 12;

$n$ is an integer from 4 to 9; and $m$ is an integer from 2 to 8.

7. The pharmaceutical composition of claim 6, wherein $R_1$, $R_2$ and $R_3$ are independently selected from the group consisting of butanediol, hexanediol, neopentyl glycol, diethylene glycol, trimethylol propane and pentaerythritol.

8. The pharmaceutical composition of claim 1, wherein the polymer matrix comprises a polymer having the formula $(C_6H_{10}O_2)_x \cdot (C_5H_8O_4)$ where x is such that the polymer has an average molecular weight of about 1000.

9. The pharmaceutical composition of claim 1, wherein the ophthalmic drug has anti-infective or anti-allergic properties.

10. The pharmaceutical composition of claim 1, wherein the ophthalmic drug is an ocular hypotensive drug selected from the group consisting of carbonic anhydrase inhibitors; beta-blockers; prostaglandins; bradykinin agonists; rho-kinase inhibitors; C-type natriuretic peptide receptor agonists, and guanylate cyclase activators.

11. A kit comprising the composition of claim 1 and a syringe.

12. The pharmaceutical composition of claim 1, wherein the polyester polymer is at least 85 wt % of the composition.

13. The pharmaceutical composition of claim 6, wherein the polyester polymer is at least 85 wt % of the composition.

14. The pharmaceutical composition of claim 1 wherein the ophthalmic drug is for treatment of age-related macular degeneration.

15. The pharmaceutical composition of claim 13 wherein the therapeutic agent is an ophthalmic drug for treatment of age-related macular degeneration.

* * * * *